(12) United States Patent
Sato et al.

(10) Patent No.: US 7,331,996 B2
(45) Date of Patent: Feb. 19, 2008

(54) INTERVERTEBRAL SPACER

(75) Inventors: Shigenobu Sato, Sapporo (JP); Kazuya Oribe, Tokyo (JP); Hiroshi Takamido, Nagoya (JP)

(73) Assignee: Showa Ika Kohgyo Co., Ltd., Aichi (JP)

( * ) Notice: Subject to any disclaimer, the term of this patent is extended or adjusted under 35 U.S.C. 154(b) by 0 days.

(21) Appl. No.: 10/642,756

(22) Filed: Aug. 19, 2003

(65) Prior Publication Data

US 2004/0102847 A1 May 27, 2004

(30) Foreign Application Priority Data

Aug. 20, 2002 (JP) ............... P2002-239086

(51) Int. Cl.
*A61F 2/44* (2006.01)
(52) U.S. Cl. .................... 623/17.16
(58) Field of Classification Search ........ 623/17.16, 623/17.11, 17.12–17.15
See application file for complete search history.

(56) References Cited

U.S. PATENT DOCUMENTS

| 4,349,921 | A | * | 9/1982 | Kuntz | 623/17.16 |
| 5,397,364 | A | | 3/1995 | Kozak et al. | |
| 5,425,772 | A | * | 6/1995 | Brantigan | 623/17.11 |
| 5,658,336 | A | * | 8/1997 | Pisharodi | 623/17.16 |
| 5,716,415 | A | * | 2/1998 | Steffee | 623/17.16 |
| 5,766,252 | A | * | 6/1998 | Henry et al. | 623/17.16 |
| 5,888,224 | A | * | 3/1999 | Beckers et al. | 623/17.16 |
| 6,080,158 | A | * | 6/2000 | Lin | 606/61 |
| 6,093,207 | A | * | 7/2000 | Pisharodi | 623/17.16 |
| 6,241,771 | B1 | | 6/2001 | Gresser et al. | |
| 6,277,149 | B1 | * | 8/2001 | Boyle et al. | 623/17.16 |
| 6,325,827 | B1 | * | 12/2001 | Lin | 623/17.16 |
| 6,500,206 | B1 | | 12/2002 | Bryan | |
| 2002/0058950 | A1 | | 5/2002 | Winterbottom et al. | |
| 2004/0199251 | A1 | * | 10/2004 | McCombe et al. | 623/17.11 |

FOREIGN PATENT DOCUMENTS

| JP | 9-503416 | 4/1997 |
| JP | 2002-95685 | 4/2002 |
| WO | 02/03895 | 1/2002 |

OTHER PUBLICATIONS

English Language Abstract of JP 2002-95685.

\* cited by examiner

*Primary Examiner*—Alvin J. Stewart
(74) *Attorney, Agent, or Firm*—Greenblum & Bernstein, P.L.C.

(57) ABSTRACT

The upper and lower surfaces 5 and 7 of an intervertebral spacer 1 inserted between the vertebrae of a spine are formed in the shape of a curved surfaces 21A and 21B each having a top portion at the middle portion in the back and forth direction. The above-mentioned upper and lower surfaces 5 and 7 are provided with a plurality of claw portions 17 for preventing withdrawal. Further, the intervertebral spacer 1 is formed in such a way that a tip portion in the direction of insertion is tapered.

5 Claims, 3 Drawing Sheets

US 7,331,996 B2

INTERVERTEBRAL SPACER

CROSS REFERENCE TO RELATED APPLICATIONS

This application is based upon and claims the benefit of priority from the prior Japanese Patent Applications No. P2002-239086 filed on Aug. 20, 2002; the entire contents of which are incorporated herein by reference.

BACKGROUND OF THE INVENTION

1. Field of the Invention

The invention relates to an intervertebral spacer that is inserted between vertebrae, after an intervertebral disk is previously removed, to thereby be put into contact in almost whole area with an end plate of the vertebra.

2. Description of the Related Art

There have been known intervertebral spacers inserted between the vertebrae the intervertebral disk of which is removed. Japanese Patent Application Laid-Open No. 2002-95685 (hereinafter referred to as a related art) shown in FIGS. 1A to 1C discloses one example of conventional intervertebral spacers.

As shown in FIG. 1A, a thickness of a rear side 101 of an intervertebral spacers 100 is larger than that of a front side 103 of an intervertebral spacers 100. An upper surface 105U and a lower surface 105L of the intervertebral spacers 100 are slanting each other, and are flat planes. Each of the slanting upper and lower surfaces 105U and 105L has a plurality of conical protruding portions 107. The intervertebral spacer 100, as shown in FIGS. 1B and 1C, is inserted between vertebrae 109A and 109B from a posterior side after an intervertebral disk is removed.

In the related art, the protruding portions 107 enhance an effect of preventing the intervertebral spacer 100 from coming off. However, the intervertebral spacer 100 has the following problems: since the front side 103 of the spacer 100 is thicker than that of the rear side 101, when the intervertebral spacer 100 is inserted between the upper and lower vertebrae 109A and 109B, it is hard to insert; further, since the upper and lower surfaces 105U and 105L are slanting each other, the end plates of the upper and lower vertebrae 109A and 109B are not put into whole surface contact with the upper and lower surfaces 105U and 105L. Hence, the contact area between them becomes small, so that the intervertebral spacer 100 can not sufficiently fix the vertebrae 109a and 109B.

SUMMARY OF THE INVENTION

This invention has been made to solve the problems. According to the aspect of the invention, there is provided an intervertebral spacer that is inserted between the vertebrae of a spine and includes a main body and withdrawal prevention means formed on the upper and lower surfaces, and formed in asymmetrically in a sectional side view, wherein the withdrawal prevention means comprises a plurality of linear claw portions formed from one side surface of the main body to the other side surface.

DETAILED DESCRIPTION OF THE INVENTION

First Embodiment

Figure 1A:
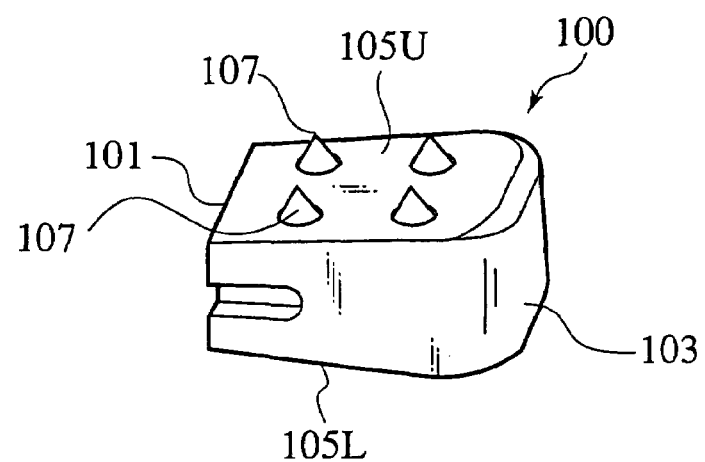
FIG. 1A is a perspective view of a conventional intervertebral spacer.
Figure 1B:
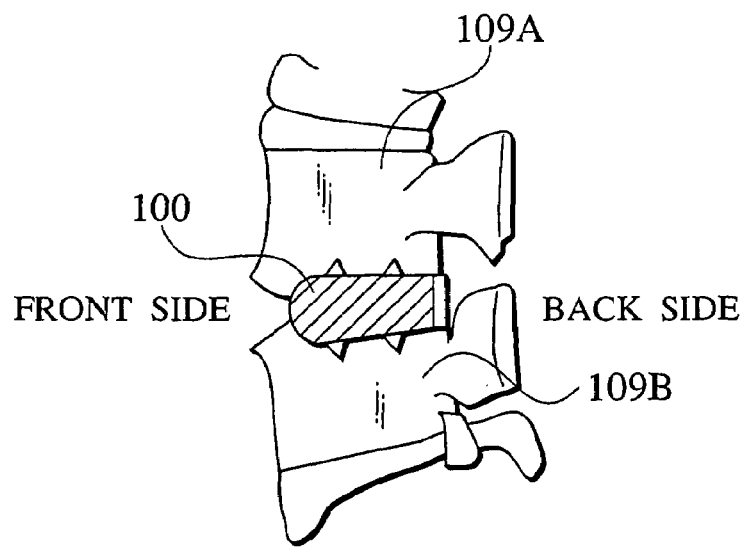
FIG. 1B is a side view of the conventional intervertebral spacer inserted between the vertebrae.
Figure 1C:
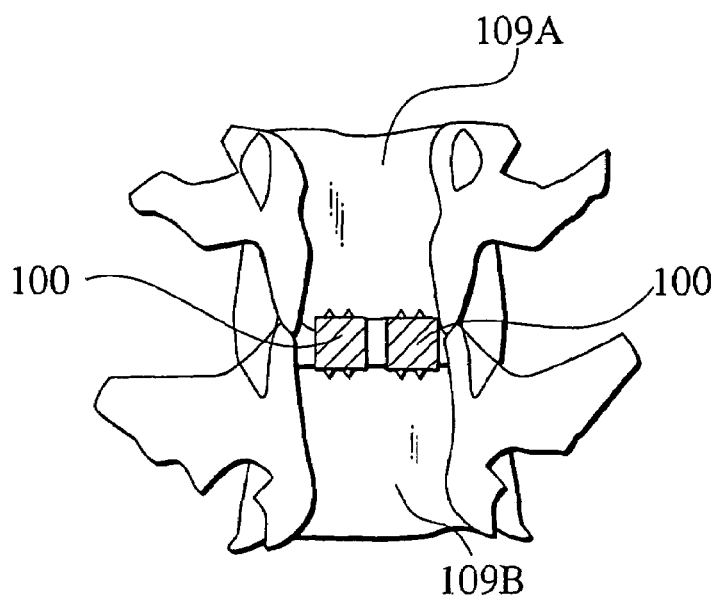
FIG. 1C is a front view of the conventional intervertebral spacer inserted between the vertebrae.
Figure 2A:
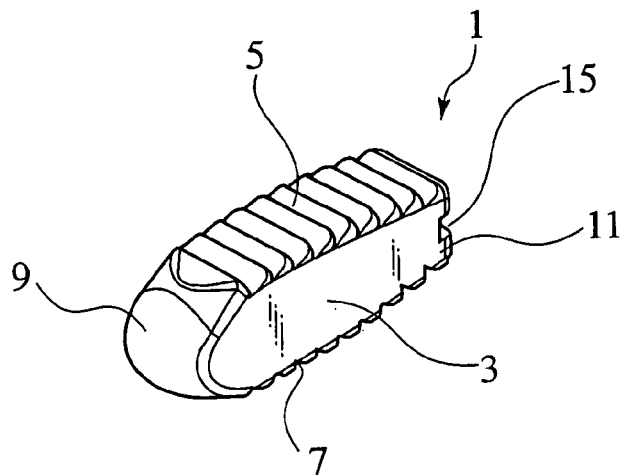
FIG. 2A is a perspective view of an intervertebral spacer according to a first embodiment of the present invention.
Figure 2B:
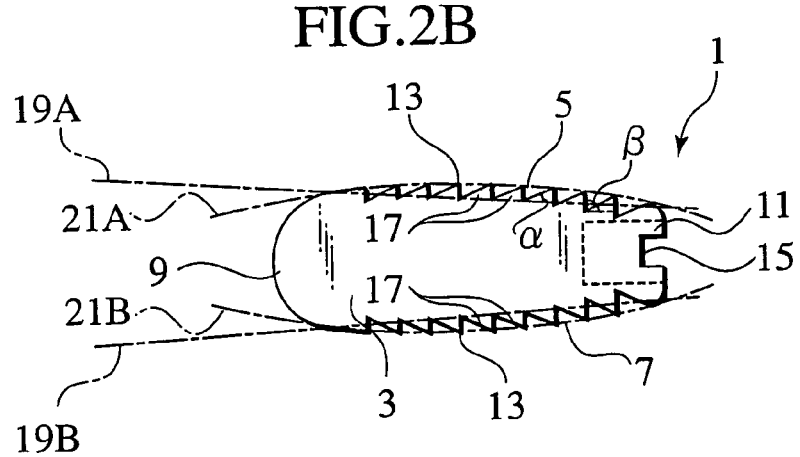
FIG. 2B is a sectional side view of the intervertebral spacer according to the first embodiment of the present invention.
Figure 2C:
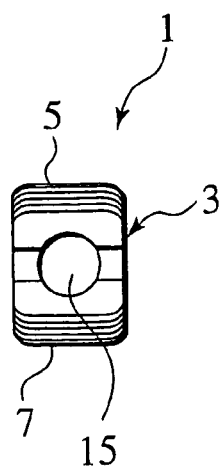
FIG. 2C is a rear view of the intervertebral spacer according to the first embodiment of the present invention.

As shown in FIGS. 2A to 2C, an intervertebral spacer 1 according to a first embodiment of the present invention is inserted between the vertebrae (not shown) after an intervertebral disk is removed.

A front end portion 9 of the main body 3 is formed in a tapered curved surface, for example, a spherical surfaces such that its forefront side gradually becomes small. In a rear end portion 11 of the main body 3, a tool engagement portion 15 is provided. A tool such as a pair of forceps is engaged with the tool engagement portion 15 when the intervertebral spacer 1 is inserted between the vertebrae.

On an upper surface 5 and a lower surface 7 of the main body 3, from one side of the intervertebral spacer 1 to the other side, claw portions 17 for preventing withdrawal are formed. Each claw portion 17 is formed in the shape of a triangle in cross section in the direction of insertion, in which a slanting angle α in the direction of insertion is small and a slanting angle β in the direction of withdrawal is larger than the slanting angle α so that the intervertebral spacer 1 can be easily inserted when it is inserted between the vertebrae and is hard to remove when it is removed.

In the main body 3, the claw portions 17 on the upper and lower surfaces 5 and 7 are arranged along imaginary slanting planes 19A and 19B slanting in such a way that the distance between the upper surface 5 and the lower surface 7 becomes narrower in the rear side 11 than in the front side 9. The ridges (vertexes) of the claw portions 17 are arranged along a curved surface 21A (or 21B), and the top portion of the claw portions 17 is positioned at the middle portion in the cross direction of the main body 3. The front portion 9 formed in the tapered curved surface protrudes from near the portions where the slanting surfaces 19A and 19B cross the curved surfaces 21A and 21B at the front end side. The rear end surface is positioned near the portions where the slanting surfaces 19A and 19B cross the curved surfaces 21A and 21B at the rear end side.

As is the case with the related art, the front end portion 9 of the main body 3 is inserted between the vertebrae from the rear side of the vertebrae after the intervertebral disk is removed. At this time, since the front end portion 9 is formed in the tapered curved surface and the slanting angle α of the claw portions 17 is small, the main body 3 can be easily inserted between the vertebrae.

After the main body 3 is inserted, the vertebrae sandwiching the main body 3 are fixed to each other by implants or the like (not shown) so that they do not move. At this time, the plurality of upper and lower claw portions 17 on the main body 3 bite into the upper and lower vertebrae to produce an effect of preventing withdrawal. And the ridges of the plurality of claw portions 17 are put into contact with almost all the surfaces of end plates of the upper and lower vertebrae because the ridges are formed along the arc-shaped curved surfaces 21A and 21B the top portions of which are positioned at the middle portion in the cross direction of the main body 3. For this reason, the intervertebral spacer 1 is sufficiently fixed between the vertebrae to thereby solve the problems of the related art.

Figure 3A:
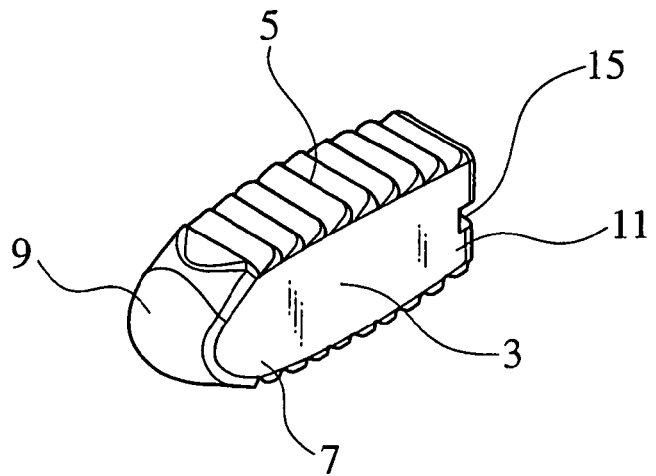
FIG. 3A is a perspective view of an intervertebral spacer according to a second embodiment of the present invention.
Figure 3B:
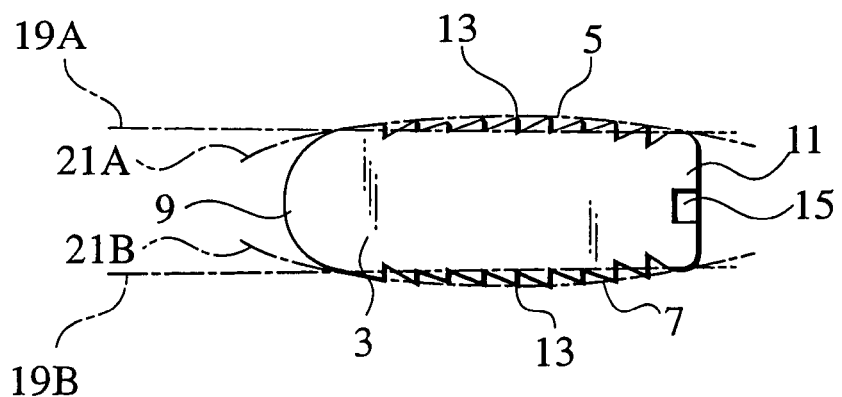
FIG. 3B is a sectional side view of the intervertebral spacer according to the second embodiment of the present invention.
Figure 3C:
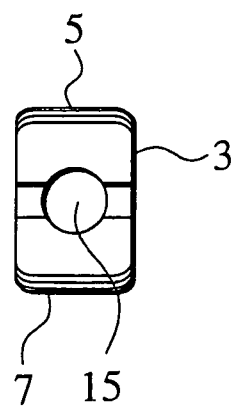
FIG. 3C is a rear view of the intervertebral spacer according to the second embodiment of the invention.

FIGS. 3A to 3C show a second embodiment of the present invention. The constituent parts performing the same functions as the constituent parts shown in the first embodiment are denoted by the same reference symbols and their descriptions will be omitted.

This second embodiment is different from the first embodiment in the point that the imaginary slanting planes 19A and 19B are formed in planes 23A and 23B parallel to each other and is the same in the other points of construction as the first embodiment.

This second embodiment can produce the same effect as the first embodiment.

What is claimed is:

1. An intervertebral spacer inserted between vertebrae of a spine, comprising:
    a body defined by a pair of upper and lower surfaces, a pair of side surfaces connected to the upper and lower surfaces, a front end side of the intervertebral spacer, and a rear end side of the intervertebral spacer; and
    a withdrawal preventer formed on the upper and lower surfaces of the body, and formed asymmetrically in a sectional side view,
    wherein the withdrawal preventer comprises a plurality of linear claw portions continuously extending from one of said pair of side surfaces of the body to the other of said pair of side surfaces of the body and continuously extending from said front end side of the body to said rear end side of the body, each of the plurality of claw portions having a vertex, with the respective vertexes arranged along a curved surface formed to extend generally longitudinally of the body, the upper and lower surfaces of the body slant such that a distance between the upper and lower surfaces at the front side of the intervertebral spacer is greater than a distance between the upper and lower surfaces at the rear side of the intervertebral spacer, and each claw portion is formed in an asymmetric triangle shape, in a section side view, defined by a first surface extending in the direction in which the intervertebral spacer is inserted, a second surface connected to a rear side of the first surface and one of the upper surface and the lower surface of the body.

2. The intervertebral spacer according to claim 1, wherein said intervertebral spacer is formed in a curved shape and a height of the middle of the spacer is greater than a height of at least one end of the spacer.

3. The intervertebral spacer according to claim 2, wherein the body is configured to have a shape of a curved surface on an insertion side such that it is tapered on the insertion side as compared with a rear side.

4. The intervertebral spacer according to claim 1, wherein an angle between the first surface of the claw portion and one of the upper surface and the lower surface of the body is larger than an angle between the second surface of the claw portion and one of the upper surface and the lower surface of the body.

5. An intervertebral spacer inserted between vertebrae of a spine, comprising:
    a body defined by a pair of upper and lower surfaces, a pair of side surfaces connected to the upper and lower surfaces, a front end side of the intervertebral spacer, and a rear end side of the intervertebral spacer; and
    a withdrawal preventer formed on the upper and lower surfaces of the body, and formed asymmetrically in a sectional side view,
    wherein the withdrawal preventer comprises a plurality of linear claw portions extending from one of said pair of side surfaces of the body to the other of said pair of side surfaces of the body and extending from said front end side of the body to said rear end side of the body, each of the plurality of claw portions having a vertex, with the respective vertexes arranged along a curved surface formed to extend generally longitudinally of the body, the upper and lower surfaces of the body slant such that a distance between the upper and lower surfaces at the front side of the intervertebral spacer is greater than a distance between the upper and lower surfaces at the rear side of the intervertebral spacer.

* * * * *